United States Patent
Britz-McKibbin

(10) Patent No.: US 10,426,751 B2
(45) Date of Patent: Oct. 1, 2019

(54) ALLOSTERIC ACTIVATORS FOR TREATMENT OF PHENYLKETONURIA

(71) Applicant: MCMASTER UNIVERSITY, Hamilton (CA)

(72) Inventor: Philip Britz-McKibbin, Hamilton (CA)

(73) Assignee: McMaster University, Hamilton, Ontario (CA)

( * ) Notice: Subject to any disclaimer, the term of this patent is extended or adjusted under 35 U.S.C. 154(b) by 0 days.

(21) Appl. No.: 15/542,225

(22) PCT Filed: Jan. 8, 2016

(86) PCT No.: PCT/CA2016/050017
§ 371 (c)(1),
(2) Date: Jul. 7, 2017

(87) PCT Pub. No.: WO2016/109899
PCT Pub. Date: Jul. 14, 2016

(65) Prior Publication Data
US 2018/0064672 A1  Mar. 8, 2018

Related U.S. Application Data

(60) Provisional application No. 62/101,403, filed on Jan. 9, 2015.

(51) Int. Cl.
*A61K 31/215* (2006.01)
*A61K 31/192* (2006.01)
*C12Q 1/26* (2006.01)

(52) U.S. Cl.
CPC .......... *A61K 31/215* (2013.01); *A61K 31/192* (2013.01); *C12Q 1/26* (2013.01); *C12Y 114/16001* (2013.01)

(58) Field of Classification Search
CPC .......................... A61K 31/215; A61K 31/192
See application file for complete search history.

(56) References Cited

U.S. PATENT DOCUMENTS

2013/0108694 A1    5/2013  Chou et al.

FOREIGN PATENT DOCUMENTS

EP        1808085        7/2007
WO     2004/064757      8/2004
(Continued)

OTHER PUBLICATIONS

Kramer et al., Metabolic Engineering, 2003;5:277-283.*
(Continued)

*Primary Examiner* — San Ming R Hui
(74) *Attorney, Agent, or Firm* — Gowling WLG (Canada) LLP

(57) ABSTRACT

A method of restoring activity in phenylalanine hydroxylase is provided. The method comprises exposing the phenylalanine hydroxylase to shikimic acid, a functionally equivalent analog thereof, a pharmaceutically acceptable salt of shikimic acid or analog thereof, or combinations thereof. A method of screening for allosteric activators for a target enzyme is also provided comprising the steps of: denaturing the target enzyme with a first chaotropic agent to yield denatured enzyme, incubating the denatured enzyme with a candidate compound under denaturing conditions to allow enzyme refolding, and assaying enzyme activity in the presence of enzyme substrate and a candidate compound; and if enzyme activity of the denatured enzyme was restored in step i) by at least about 10% of residual enzyme activity, denaturing the target enzyme with a second chaotropic agent to yield denatured enzyme, incubating the denatured enzyme with the candidate compound under non-denaturing conditions to allow enzyme refolding, and assaying enzyme (Continued)

activity in the presence of enzyme substrate and the candidate compound, wherein an increase in enzyme activity of at least about 10% of residual enzyme activity indicates that the candidate compound is an allosteric activator of the target enzyme.

9 Claims, 6 Drawing Sheets

(56) References Cited

FOREIGN PATENT DOCUMENTS

| WO | 2005/049000 | 6/2005 |
| WO | 2008/153771 | 12/2008 |
| WO | 2011/097335 | 8/2011 |

OTHER PUBLICATIONS

Wong et al., Antiviral Research, 2009;83:!86-190.*
Heintz et al., Human Mutat, 2013;34:927-936.*
International Search Report of PCT/CA2016/050017.
Written Opinion of PCT/CA2016/050017 dated Mar. 23, 2016.
Camp, K. et al., Molecular Genetics and Metabolism, Mar. 6, 2014 (Mar. 6, 2016), 112, pp. 87-112.
Santos-Sierra, S., et al., Human Molecular Genetics, Jan. 13, 2012 (Jan. 13, 2012), 21/8, pp. 1877-1887.
Partial Supplementary European Search Report—dated Jun. 29, 2018.
Database WPI , Week 201247 Thomson Scientific, London, GB; AN 2012-J00937 XP002782152, & JP 2012 131760 A (Shonan Yobo Ikaaku Kendyusho YG) Jul. 12, 2012 (2012-07-012) *abstract*.
Database WPI, Week 200975; Thompson Scientific, London, GB; AN 2009-005782; XP002782153 & CN 101 549 069 (Ding D) Oct. 7, 2009 (Oct. 7, 2010) *abstract*.
Database WPI. Week 201366; Thompson Scientific, London, GB; AN 2013-P86336 XP002782154 & CN103 054 848 A (Chengdu Kanghong PHarm Co Ltd) Apr. 24, 2013 (Apr. 24, 2013) *abstract*.

* cited by examiner

US 10,426,751 B2

ALLOSTERIC ACTIVATORS FOR TREATMENT OF PHENYLKETONURIA

FIELD OF THE INVENTION

The present invention is related to small molecules that function as allosteric activators of mutant enzymes for treating genetic disorders based on enzyme enhancement therapy, and in particular, to pharmacological chaperones useful for the treatment of phenylketonuria (PKU).

BACKGROUND OF THE INVENTION

Phenylalanine hydroxylase (PAH) is a multimeric hepatic enzyme that catalyzes the hydroxylation of L-phenylalanine (Phe) to L-tyrosine (Tyr) in the presence of iron, molecular oxygen and a redox-active cofactor, tetrahydrobiopterin (BH4). Phenylketonuria (PKU) is a heterogeneous group of disorders that can lead to intellectual disability, seizures, and impaired growth and development in affected children if left untreated with an average reported incidence rate of 1:12,000 in North America. PKU is a common in-born error of amino acid metabolism that is related to more than 500 disease-causing mutations of PAH or by a defect in the synthesis or regeneration of BH4. Due to the great allelic variation and large number of pathogenic mutations, universal newborn screening (NBS) for PKU relies on tandem mass spectrometry to detect hyperphenylalaninaemia in the population from dried blood spot extracts with follow-up diagnostic testing by quantitative analysis of plasma Phe and Tyr. Several PAH mutations have been shown to affect protein folding in the endoplasmic reticulum resulting in accelerated degradation and/or aggregation due to missense mutations (63%) and small deletions (13%) in protein structure that attenuates or largely abolishes enzyme catalytic activity. In general, three major phenotypic groups are classified in PKU based on Phe levels measured at diagnosis, dietary tolerance to Phe and potential responsiveness to BH4 therapy, including classical PKU (Phe>1200 µM), atypical or mild PKU (Phe is 600-1200 µM) and permanent mild hyperphenylalaninaemia (HPA, Phe<600 µM).

Currently, lifelong dietary restriction of Phe and BH4 supplementation are the only two available treatment options for PKU, where early therapeutic intervention is critical to ensure optimal clinical outcomes in affected infants. However, costly medication and special low-protein foods imposes a major burden on patients that can lead to malnutrition, psychosocial or neurocognitive complications notably when these products are not fully covered by private health insurance. Moreover, BH4 therapy is primarily effective for treatment of mild hyperphenylalaninaemia as related to defects in BH4 biosynthesis, whereas only 20-30% of patients with mild or classical PKU are responsive. Thus, there is an urgent need for new treatment modalities for PKU as an alternative to burdensome Phe-restriction diets, including large neutral amino acid formulations and enzyme replacement therapy using PEGylated recombinant phenylalanine ammonia lyase.

Thus, it would be desirable to develop an alternative method for the treatment of phenylketonuria.

SUMMARY OF THE INVENTION

Novel chaperones for phenylalanine hydroxylase are herein described that are useful to treat protein misfolding and enzyme deficiency disorders, such as phenylketonuria.

Thus, in one aspect of the present invention, a method of restoring phenylalanine hydroxylase activity is provided comprising exposing a mutant phenylalanine hydroxylase to shikimic acid or a functionally equivalent analogue thereof.

In another aspect of the invention, a method of treating phenylketonuria in a mammal is provided comprising administering to the mammal a therapeutically effective amount of shikimic acid or a functionally equivalent analogue thereof.

In another aspect, a composition is provided comprising shikimic acid, a functionally equivalent analogue thereof, a pharmaceutically acceptable salt of shikimic acid or analogue thereof, or combinations thereof, further combined with a second therapeutic agent that is also useful to treat phenylketonuria or symptoms thereof.

In a further aspect of the invention, a method of screening for pharmacological chaperones for a target enzyme is provided. The method includes a A method of screening for allosteric activators for a target enzyme comprising:

i) denaturing the target enzyme with a first chaotropic agent to yield denatured enzyme, incubating the denatured enzyme with a candidate compound under denaturing conditions to allow enzyme refolding, and assaying enzyme activity in the presence of enzyme substrate and a candidate compound; and ii) if enzyme activity of the denatured enzyme is restored in step i) by at least about 10% of residual enzyme activity, denaturing the target enzyme with a second chaotropic agent to yield denatured enzyme, incubating the denatured enzyme with the candidate compound under non-denaturing conditions to allow enzyme refolding, and assaying enzyme activity in the presence of enzyme substrate and the candidate compound, wherein an increase in enzyme activity of at least about 10% residual enzyme activity indicates that the candidate compound is an allosteric activator of the target enzyme.

These and other aspects of the invention are described in the following description by reference to the drawings.

DETAILED DESCRIPTION OF THE INVENTION

Figure 1:
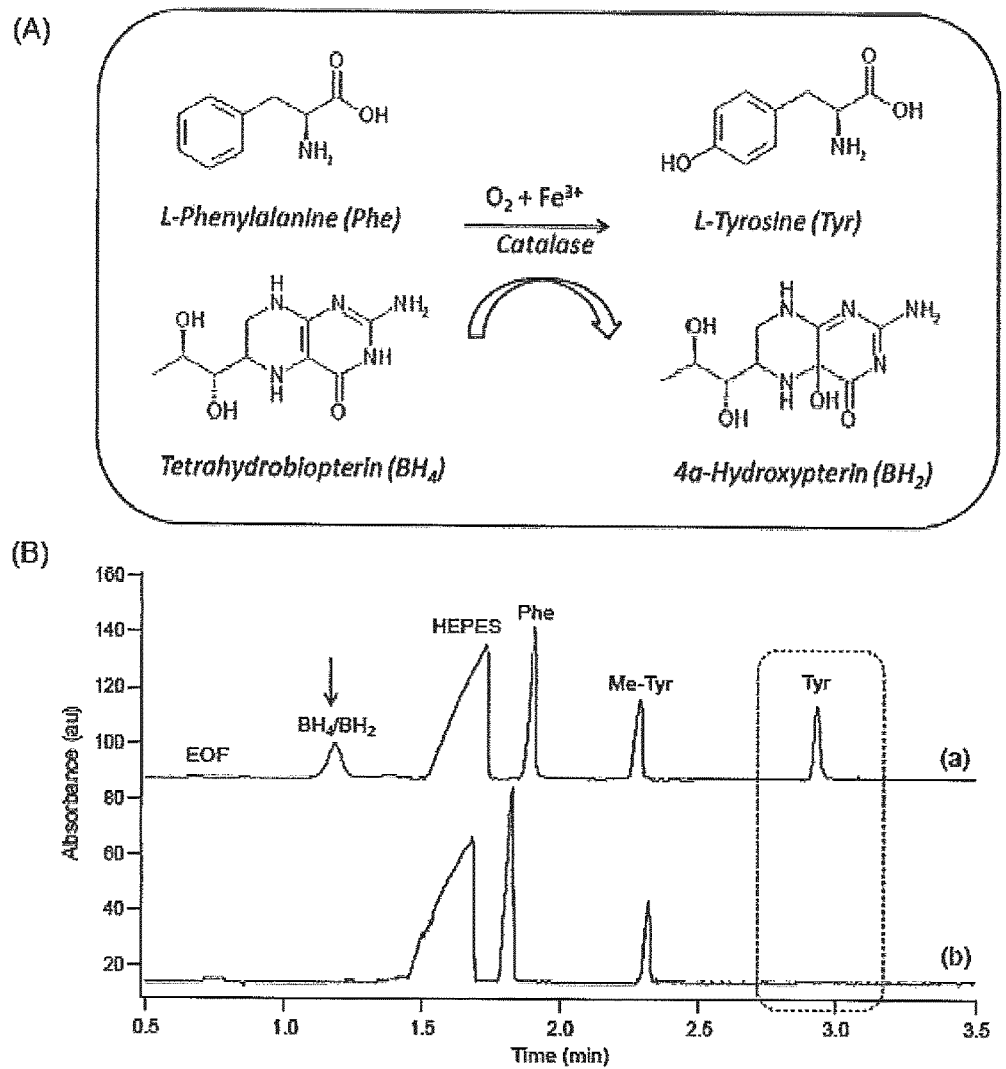
FIG. 1 illustrates (A) a schematic of the PAH enzymatic reaction, and (B) an electropherogram overlay depicting (a) resolution of major components in a PAH-catalyzed enzymatic reaction relative to (b) a negative control without addition of BH4 and DTT, where no product (Tyr) is detected. All separations were performed using a BGE of 200 mM borate, pH 10.3 using a voltage of 30 kV with UV detection at 200 nm, whereas enzyme reactions were performed off-line in 20 mM HEPES, 200 mM NaCl, pH 7.0.

A method of restoring phenylalanine hydroxylase activity in a mutant phenylalanine hydroxylase enzyme is provided. In this regard, mutant phenylalanine hydroxylase may be combined with shikimic acid or a functionally equivalent analogue thereof to restore hydroxylase activity to the mutant enzyme.

The term "mutant" as used herein with respect to phenylalanine hydroxylase is a form of the enzyme which does not exhibit endogenous hydroxylase activity, and may include denatured or otherwise disrupted enzyme, as well as mutated enzyme in which one or more amino acids have been altered from the wild-type enzyme to yield an enzyme which does not exhibit endogenous hydroxylase activity. Examples of the mutant phenylalanine hydroxylase mutants include the I65T mutant (in which the amino acid at position 65 of the enzyme is altered from isoleucine to threonine) and the R261Q mutant (in which the amino acid at position 261 is altered from arginine to glutamine). Other mutants include missense or deletion mutations associated with the regulatory and catalytic domains of PAH.

Shikimic acid, or (3R,4S,5R)-3,4,5-trihydroxycyclohex-1-ene-1-carboxylic acid, and functionally equivalent analogues thereof are useful in the present method. The term "analogue" refers to naturally or non-naturally occurring analogues of shikimic acid. Such functionally equivalent analogues of shikimic acid include, for example, analogues having one or more additional substituents on the cyclohexene ring of shikimic acid, analogues in which the cyclohexene ring of shikimic acid is replaced with a cyclohexane ring, and analogues in which one or more of the hydroxyl groups on the cyclohexene ring is substituted. Preferred analogues are those which maintain the polyol stereochemistry and acidity of the carboxylic acid, and/or analogues which may have more desirable characteristics than shikimic acid for use in a therapeutic sense, for example, increased activity and/or stability.

In one embodiment, a suitable analogue of shikimic acid is an analogue having one or more additional substituents on the cyclohexene ring. This additional substituent may be at any position on the ring, e.g. on the carbon at positions 1 to 6. If the substituent is at position 1 or 6, the double bond of the cyclexene ring is removed by reduction, and the ring becomes a cyclohexane ring. Examples of suitable substituents for addition to the ring include hydroxyl, thio, —$OR^1$, —$NH_2$, $NO_2$, —$NHR^1$, —$NR^1R^2$, —$SR^1$ and a $C_1$-$C_6$ branched or unbranched alkyl group such as methyl, ethyl, propyl, isopropyl, butyl, isobutyl, pentyl and the like, $C_1$-$C_6$ alkoxy, or $C_1$-$C_6$ alkanol, wherein $R^1$ and $R^2$ are independently selected from the group consisting of $C_1$-$C_6$ alkyl, $C_1$-$C_6$ alkanol and $C_1$-$C_6$ alkoxy.

In another embodiment, a suitable analogue of shikimic acid is an analogue in which one or more of the hydroxyl groups on the cyclohexene ring is substituted. Examples of suitable substituents for addition to the ring include hydrogen, thio, $C_1$-$C_6$ alkyl, $C_1$-$C_6$ alkanol, $C_1$-$C_6$ alkoxy, —$OR^1$, —$NH_2$, $NO_2$, —$NHR^1$, —$NR^1R^2$, and —$SR^1$, wherein $R^1$ and $R^2$ are independently selected from the group consisting of $C_1$-$C_6$ alkyl, $C_1$-$C_6$ alkanol and $C_1$-$C_6$ alkoxy.

In another embodiment, a suitable analogue of shikimic acid is an analogue in which the stereochemistry of one or more of the hydroxyl groups on the cyclohexene ring is substituted or new stereogenic centres are introduced. Examples of suitable changes include different R/S-configurations of the hydroxyl or other groups on the ring structure of shikimic acid or analogues thereof, or the introduction of new stereogenic centres following reduction of the double bond on shikimic acid.

Functionally equivalent salts of shikimic acid and analogues thereof may also be utilized in the present method. A "pharmaceutically acceptable salt" refers to a salt that essentially retains the desired biological activity of the parent compound and which does not impart unacceptable toxicological effects. Examples of such salts include acid addition salts and base addition salts. Acid addition salts include those derived from nontoxic inorganic acids, such as hydrochloric, nitric, phosphoric, sulfuric, hydrobromic, hydroiodic, phosphorous and the like, as well as from nontoxic organic acids such as aliphatic mono- and dicarboxylic acids, phenyl-substituted alkanoic acids, hydroxy alkanoic acids, aromatic acids, aliphatic and aromatic sulfonic acids and the like. Base addition salts include those derived from alkaline earth metals, such as sodium, potassium, lithium, magnesium, calcium and the like, as well as from nontoxic organic amines, such as N,N'-dibenzylethylenediamine, N-methylglucamine, chloroprocaine, choline, diethanolamine, ethylenediamine, procaine and the like.

A preferred analogue of shikimic acid for use in the present method is a naturally occurring cyclitol which includes an additional substituent at position 1 of the shikimic acid ring following reduction of the double bond to yield a cyclohexane ring. One such analogue is D-quinic acid, or a pharmaceutically acceptable salt thereof, in which the additional substituent is a hydroxyl group.

The term "functionally equivalent" refers herein to compounds, e.g. analogues and salts of shikimic acid, which retain the biological activity of shikimic acid, e.g. to restore hydroxylase activity in phenylalanine hydroxylase. The analogue or salt need not exhibit identical activity to shikimic acid, but will exhibit sufficient activity to render it useful to restore hydroxylase activity in phenylalanine hydroxylase, e.g. at least about 25% of the biological activity of shikimic acid, and preferably at least about 50% or greater of the biological activity of shikimic acid.

Shikimic acid, D-quinic acid and analogues thereof may be chemically synthesized or may alternatively be isolated from various autotrophic organisms. For example, shikimic acid may be extracted from plants such as *Illicium verum*, from the seeds of the *Liquidambar styraciflua* fruit or from the needles of several varieties of pine tree. In addition, biosynthetic pathways in some bacteria, such as *E. coli*, may be used to synthesize shikimic acid. Similarly, shikimic acid analogues such as D-quinic acid may be obtained from cinchona bark, coffee beans, and other plant products. D-quinic acid may alternatively be made synthetically by hydrolysis of chlorogenic acid.

The present method encompasses the treatment of a phenylketonuria in a mammal. The terms "treat", "treating" and "treatment" are used broadly herein to denote methods that favorably alter the targeted disorder, including those that moderate or reverse the progression of, reduce the severity of, or prevent, the disorder. The term "mammal" is used herein to encompass both human and non-human mammals.

Shikimic acid, D-quinic acid or functionally equivalent salts or analogues thereof, may be administered either alone or in combination with at least one pharmaceutically acceptable adjuvant, in the treatment of phenylketonuria in an embodiment of the invention. The expression "pharmaceutically acceptable" means acceptable for use in the pharmaceutical or veterinary arts, i.e. not being unacceptably toxic or otherwise unsuitable. Examples of pharmaceutically acceptable adjuvants are those used conventionally with peptide- or nucleic acid-based drugs, such as diluents, excipients and the like. Reference may be made to "Remington's: The Science and Practice of Pharmacy", 21st Ed., Lippincott Williams & Wilkins, 2005, for guidance on drug formulations generally. The selection of adjuvant depends on the intended mode of administration of the composition. In one embodiment of the invention, the compounds are formulated for administration by infusion, or by injection either subcutaneously or intravenously, and are accordingly utilized as aqueous solutions in sterile and pyrogen-free form and optionally buffered or made isotonic. Thus, the compounds may be administered in distilled water or, more desirably, in saline, phosphate-buffered saline or 5% dextrose solution. Compositions for oral administration via tablet, capsule or suspension are prepared using adjuvants including sugars, such as lactose, glucose and sucrose; starches such as corn starch and potato starch; cellulose and derivatives thereof, including sodium carboxymethylcellulose, ethylcellulose and cellulose acetates; powdered tragancanth; malt; gelatin; talc; stearic acids; magnesium stearate; calcium sulfate; vegetable oils, such as peanut oils, cotton seed oil, sesame oil, olive oil and corn oil; polyols such as propylene glycol, glycerine, sorbital, mannitol and polyethylene glycol; agar; alginic acids; water; isotonic saline and phosphate buffer solutions. Wetting agents, lubricants such as sodium lauryl sulfate, stabilizers, tableting agents, antioxidants, preservatives, colouring agents and flavouring agents may also be present. Creams, lotions and ointments may be prepared for topical application using an appropriate base such as a triglyceride base. Such creams, lotions and ointments may also contain a surface active agent. Aerosol formulations may also be prepared in which suitable propellant adjuvants are used. Other adjuvants may also be added to the composition regardless of how it is to be administered, for example, anti-microbial agents may be added to the composition to prevent microbial growth over prolonged storage periods.

To treat phenylketonuria, a therapeutically effective amount of shikimic acid or a salt or analogue thereof, or combinations of these, is administered to a mammal. The term "therapeutically effective amount" is used herein to refer to an amount of shikimic acid, or salt or analogue thereof, effective to restore phenylalanine hydroxylase activity, while not exceeding an amount which may cause significant adverse effects. Dosages of shikimic acid, salts or analogues thereof that are therapeutically effective will vary with many factors including the nature of the condition to be treated, as well as the particular individual being treated. Appropriate dosages for use include dosages sufficient to restore at least about a 10% of phenylalanine hydroxylase activity in a mammal being treated, and preferably restore greater than 10% phenylalanine hydroxylase activity, e.g. at least about 20%, 30%, 40%, 50% or greater. The term "restore" used herein with respect to phenylalanine hydroxylase activity refers to an increase in phenylalanine hydroxylase activity from the endogenous or baseline phenylalanine hydroxylase activity in the mammal prior to treatment. In one embodiment, dosages within the range of about of 0.2 µM to 20 mM are appropriate.

In the present treatment, shikimic acid, salt or analogue thereof, or combinations of these, may be administered by any suitable administrable route. Examples of suitable administrable routes include, but are not limited to, oral, subcutaneous, intravenous, intraperitoneal, intranasal, enteral, topical, sublingual, intramuscular, intra-arterial, intramedullary, intrathecal, inhalation, ocular, transdermal, vaginal or rectal means. Depending on the route of administration, the protein or nucleic acid may be coated or encased in a protective material to prevent undesirable degradation thereof on administration.

In one embodiment, the present plant-derived natural products, or functionally equivalent synthetic analogues or salts thereof, may be provided advantageously in the form of a nutritional supplement that offers a readily administrable, safe, and effective therapeutic treatment for patients with phenylketonuria (PKU). This would reduce the need for stringent and lifelong dietary restriction of phenylalanine.

As one of skill in the art will appreciate, shikimic acid or a salt or analogue thereof (including combinations), may be administered to a mammal in conjunction with a second therapeutic agent to facilitate treatment of the mammal. The second therapeutic agent may be administered simultaneously with the shikimic acid or analogue, either in combination or separately. Alternatively, the second therapeutic agent may be administered prior or subsequent to the administration of shikimic acid or analogue thereof. In one embodiment, the second therapeutic agent is an agent that is also useful to treat phenylketonuria or symptoms thereof. Examples of such second therapeutic agents include, but are not limited to, tetrahydrobiopterin (BH4) therapy (e.g. Kuvan® from Biomarin Pharmaceutical) and PEGlyated phenylalanine ammonium lyase (e.g. Pegvaliase® from Biomarin Pharmaceutical).

Thus, in another aspect of the invention, a pharmaceutical composition is provided comprising shikimic acid or a salt or analogue thereof in combination with a second therapeutic agent that is also useful to treat phenylketonuria or symptoms thereof. In embodiments, the composition may comprise shikimic acid or a salt or analogue thereof with tetrahydrobiopterin or with PEGlyated phenylalanine ammonium lyase.

The present compounds were identified using a novel screening method. In this regard, a functional two-tiered screening method has been developed for the discovery of pharmacological chaperones that function as "allosteric activators" (e.g. which bind/stabilize a target enzyme to enhance/restore activity without deleterious inhibition) and that may be used to identify chaperones for other relevant enzyme/protein targets, including those involved in amino acid deficiency disorders, lysosomal storage disorders, cystic fibrosis, as well as other human diseases associated with protein misfolding/aggregation. The two-tiered screening method includes a first step, e.g. an enzyme stabilization assay, and a second step, e.g. a chaperone assay.

In a first step of the two-tiered screening method, restoration of enzyme activity upon denaturation was used to characterize compounds that stabilize and enhance activity of a target enzyme following denaturation. Denaturation may be effected using many techniques, e.g. chemical, temperature, pH and the like. It is preferable that a denaturation method is used that does not result in aggregation/precipitation of the target enzyme. In one embodiment, chemical denaturation was employed using a first chaotropic or denaturant agent, and the enzyme remained soluble in solution. Examples of suitable chaotropic agents include butanol, ethanol, guanidinium chloride, lithium perchlorate, lithium acetate, magnesium chloride, phenol, propanol, sodium dodecyl sulfate, thiourea and urea. The target enzyme is denatured with a selected chaotropic agent such that the enzyme remains solubilised and residual enzyme activity is largely abolished (<5% residual enzyme activity remains—as compared to wild-type). The term "residual enzyme activity" refers to the net activity of the enzyme under a given condition (denaturing conditions at 6 M urea or 4 M guandinium). Residual activity is the remaining activity of the enzyme assumed after a perturbation (denaturation with chaotropic agent), while wild-type enzyme under native conditions (no denaturant) has full 100% activity.

Following denaturation, the enzyme is incubated with the candidate compound, e.g. for an amount of time sufficient to permit enzyme interaction and/or refolding, e.g. 15 minutes or less. Enzyme substrate is then added to the enzyme and candidate compound, and enzyme activity is assayed under denaturing conditions, e.g. conditions sufficient to cause denaturation, for a period of time sufficient to determine whether or not the candidate compound is capable of restoring activity of the target enzyme under denaturing conditions. Typically, the assay will measure enzyme activity by measuring the level of product generated. In the case of phenylalanine hydroxylase, L-tyrosine (Tyr) formation was measured. While many detection methods may be used (e.g., fluorescence, electrospray ionization-mass spectrometry), a capillary electrophoresis (CE) with UV absorbance assay was used herein to directly measure PAH activity without spectral interferences or ionization suppression effects. This detection method may be adapted to measure activity of a different enzyme based on formation of a product by that enzyme. In addition, the use of capillary electrophoresis provides a method that can tolerate large amounts of chaotropic agents in buffer while resolving complex sample mixtures.

If enzyme activity is restored in the first step, e.g. by at least about 10% of residual or wild-type enzyme activity, then a second step (e.g. chaperone assay) is conducted in which the target enzyme is denatured using a second chaotropic agent that is different from the first chaotropic agent (e.g, guanidium chloride), such that residual enzyme activity is largely abolished (<5% remains). Generally an amount of chaotropic agent is used to achieve suitable denaturation. Following denaturation, the target enzyme is exposed to native or non-denaturing conditions, e.g. in which the chaotropic agent is diluted and refolding of the target enzyme is achieved in the presence of the candidate compound. Enzyme activity is assayed in the presence of enzyme substrate and the candidate compound to determine if the candidate compound is capable of restoring activity of the refolded enzyme. An increase in residual target enzyme activity of at least about 10% relative to suitable controls (e.g., enzyme assayed in the absence of candidate compound, such as blank or non-selective/weak osmolyte) indicates that the candidate compound is a chaperone for the target enzyme. This functional two-tiered assay directly measures enzyme activity enhancement and, therefore, identifies small molecules that function as allosteric activators of misfolded/inactive enzymes and excludes competitive inhibitors that are undesirable as PCs.

This screening method is useful to identify allosteric activators of any target enzyme, and particularly useful to identify allosteric activators of misfolded or mutant enzymes involved in, for example, genetic diseases associated with protein misfolding and/or enzyme deficiency, including but not limited to, conditions such as phenylketonuria, maple syrup urine disease, medium chain acetylcoenzyme A dehydrogenase deficiency, galactosemia, citrullinemia, isovaleric academia, propionic acidemia, cystic fibrosis and lysosomal storage diseases such as Gaucher disease.

Embodiments of the invention are described in the following specific examples which are not to be construed as limiting.

EXAMPLE 1

The following materials and methods were employed in this example.

Chemicals and Reagents—

De-ionized water for buffer, stock, and sample preparations was obtained using a Barnstead EASYpure® II LF ultrapure water system (Dubuque, Iowa, USA). Boric acid, 4-(2-Hydroxyethyl) piperazine-1-ethanesulfonic acid (HEPES), sodium chloride (NaCl), and sodium hydroxide (NaOH) were obtained from Sigma-Aldrich (St. Louis, Mo., USA) which were used in buffer preparation and 1 M NaOH was used to adjust the pH of the assay and separation buffer. L-phenylalanine (Phe), L-tyrosine (Tyr), 3-fluoro-L-phenylalanine (F-Phe), the internal standard (IS) 3-O-methyl-L-tyrosine (Me-Tyr), shikimic acid (SA), D-quinic acid (QA), gallic acid and 3-deoxyshikimic acid (3-DSA) were all purchased from Sigma-Aldrich. Stock solutions were prepared in HEPES buffer (20 mM HEPES pH 7.0, 0.2 MNaCl) and stored refrigerated at +4° C. Chemical denaturant, urea, was purchased from Bioshop (Burlington, ON, Canada), whereas guandium hydrochloride (GndCl) was obtained from Sigma-Aldrich. Stock solutions of chemical denaturants (20M urea, 20 M GndCl) were freshly prepared each day in HEPES buffer with gentle heating. Catalase, (6R)-L-erythro-5,6,7,8-tetrahydro-L-erythro-biopterin sulfate (BH4), DL-dithiothreitol (DTT) and ammonium iron (II) sulfatehexahydrate ($Fe^{2+}$) were all purchased from Sigma-Aldrich. BH4 and D stock solutions were prepared in 0.1 M HCl and $FeSO_4$ stocks were prepared in de-ionized water. Dimethyl sulfoxide (DMSO) was purchased from Caledon Laboratories Ltd. (Georgetown, ON, Canada) and used for preparation of primary stock solutions for ligands in chemical library, as well as lead compound analogs purchased commercially. 3-amino-2-benzyl-7-nitro-4-(2-quinolyl)-1,2-dihydroisoquinolin-1-one (compound III) and (5,6-dimethyl-3-(4-methyl-2-pyridinyl)-2-thioxo-2,3-dihydrothieno[2,3-d] pyrimidin-4(1H)-one (compound IV) were donated by Dr. Martinez' laboratory (Pey et al., J. Clin. Invest., 2008, 118, 2858-2867) for validation of chaperone activity using the two-tiered screening method described herein for identification of novel PCs from a chemical library.

Chemical Library and Computational Screen for Drug-Like Activity—

A customized chemical library containing 600 unique small molecules was synthesized in the laboratory of Dr. McNulty at McMaster University. All compounds were stored refrigerated (+4° C.) in DMSO (10 mM) after spectral characterization by $^1$H-NMR and electron impact ionization (EI)-MS to confirm their purity. Lead compounds identified after primary screening were also re-synthesized to confirm their chaperone activity with WT and mutant PAHs notably for ligands stored in DMSO over several years. In-silico screen was performed using ACD Labs PhysChem Suite 2012 software for predicting drug-like properties of compounds based on Lipinski's rules of five (molecular weight (MW)<500, Log P<5, hydrogen bond donors (HBDs)<5, hydrogen bond acceptors (HBAs)<10, rotational bonds (RBs)<10)) and total polar surface area (TPSA)<120 Å (Li, Drug Discov. Today. Technol., 2005, 2, 179-85), resulting in 100 candidates for screening in order to avoid false positives due to insolubility, aggregation and/or cell toxicity. To note, this in-silico screen is different from virtual screening which focuses on the structural similarity of ligand binding environment in PAH.

Recombinant Expression of PAH in *Escherichia Coil*—

Expression of recombinant human WT-PAH and two PAH mutants (I65T and R269Q) as fusion protein with maltose-binding protein in eukaryotic cell cultures using pMAL expression vector was performed by the Martinez laboratory at the University of Bergen as described in Svebak et al., Biochem. J., 1995, 306, 589-597. Briefly, purification of the fusion proteins expressed in the pMAL vector system was performed using affinity chromatography followed by size-exclusion chromatography to remove low molecular weight components. Subsequently, the fusion proteins were cleaved by the restriction protease factor Xa and then phosphorylated by cyclic adenosine monophosphate (cAMP)-dependent protein kinase. The two clinically relevant PAH mutants, I65T and R261Q comprise single-point mutations in the regulatory and catalytic domain, respectively which are associated with highly variable phenotypes ranging from mild to classical PKU. For instance, patients with R261Q genotypes are reported to have inconsistent responses to BH4 therapy. In this work, I65T and R261Q PAH mutants were measured to have residual catalytic activities of (35±1)% and (5±0.5)% relative to WT PAH under standardized conditions (i.e., enzyme concentrations, assay buffer etc.), respectively. Stock solutions of WT-PAH and PAH mutants were prepared in enzyme reaction buffer (20 mM HEPES pH 7.0, 200 mM NaCl), and divided into separate 10 μL aliquots in 0.5 mL sterilized centrifuge tubes prior to storage at −80° C. Note that all enzyme assays were performed on aliquots of frozen enzymes thawed slowly in the fridge prior to daily use. Multiple freeze-thaw cycles of PAH were found to contribute to lower enzymatic activity, whereas all final solutions for enzyme reactions were prepared containing <1% v DMSO to prevent enzyme inactivation.

Capillary Electrophoresis (CE) Separations—

All CE separations for measuring PAH activity were performed on a Hewlett Packard 3D CE system (Agilent Technologies Inc., Waldbronn, Germany) equipped with UV photodiode array (PDA) detection. Uncoated open tubular fused-silica capillaries (Polymicro Technologies Inc., Phoenix, Ariz., USA) with dimensions of 25 μm inner diameter, 360 μm outer diameter and total capillary length of 35 cm were used for this study. New capillaries were conditioned by rinsing with methanol for 30 min, de-ionized water for 30 min, 1 M NaOH for 30 min and background electrolyte (BGE) for 60 min. The BGE used in CE separations for measuring PAH-catalyzed Tyr formation was 200 mM borate, pH 10.3. At the beginning of each day, the capillary was rinsed with 1.0 M NaOH for 10 min and BGE for 15 min. Each separation started with a pre-rinsing of the capillary with 1.0 M NaOH for 3 min and BGE for 3 min followed by hydrodynamic injection of the sample at 50 mbar for 75 s. For enzymatic assays, resolution of Phe (substrate), Tyr (product), Me-Tyr (internal standard), and reduced/oxidized cofactors, tetrahydrobiopterin (BH4) and dihydrobiopterin (BH2), were performed under an applied voltage of 30 kV using a positive gradient pressure of 20 mbar over 5.0 min with UV absorbance monitored at 200 nm. Due to the narrow optical path length (inner diameter of capillary, 25 μm) and small sample volumes typically injected on-column in CE, an on-line sample pre-concentration technique based on dynamic pH junction was developed that is compatible with the buffer conditions used in the enzyme reaction. In this case, weakly acidic metabolites within a long sample plug (75 sec) are electrokinetically focused at the boundary of a discontinuous electrolyte system comprising HEPES (pH 7.0) and borate (pH 10.3) as sample and BGE segments, respectively. The CE system stability was monitored daily by performing quality control runs of a standard sample mixture prior to enzymatic reactions.

External Calibration Curve for Measurement of Enzyme Activity—

PAH catalytic activity was measured directly by CE with UV detection based on the rate of formation of Tyr that is resolved from excess Phe and other components in the enzyme reaction. In this case, stock solution of Tyr was diluted to twelve different concentrations ranging from 2.5 to 1000 μM in the enzyme reaction buffer (20 mM HEPES and 200 mM NaCl, pH 7.0), whereas Me-Tyr was used as the internal standard (IS) at a final concentration of 100 μM. The calibration curve was generated using an average of nine replicates performed over three days (n=9) with good precision as reflected by a coefficient of variance (CV) under 5%. Overall, excellent linearity over a 400-fold concentration range was realized for calibration curves as reflected by a correlation of determination ($R^2$) of 0.9995. The limit of quantification (LOQ) and limit of detection (LOD) for Tyr when using CE with UV detection was 2.5 μM and 1 μM, respectively, based on capillary dimensions and sample injection conditions used in this work.

Enzyme Kinetics of WT and Mutant PAH—

Tetrameric human phenylalanine hydroxylase (PAH) enzyme kinetic assays were performed off-line under standardized conditions prior to quantification of Tyr formation by CE with UV detection. Enzyme assays were performed by first mixing together Phe (1 mM), catalase (100 nM) and PAH (0.25 µM/subunit) in a reaction buffer (20 mM HEPES and 200 mM NaCl, pH 7.0) that were equilibrated at 25° C. for 4 min. Then, ferrous ($Fe^{2+}$) ammonium sulfate (100 µM) was added to the solution for 1 min and the reaction was subsequently initiated by addition of BH4 (100 nM) with DTT (5 mM) using a total volume of 100 µL. The reaction mixture was then vortexed for 60 s followed by sonication for 2 min prior to centrifugation for 10 s at 4 g and storage in a refrigerator (+4° C.). An aliquot (20 µL) was withdrawn from the quenched enzyme reaction and placed in a micro vial containing Me-Tyr as IS (100 µM) prior to CE analysis. The stability of the quenched enzyme reaction was confirmed by intermittent analysis of PAH activity over 6 h at room temperature, and no significant changes in the Tyr/IS or Phe/Tyr response ratio were measured. Enzymatic reactions were performed for both WT-PAH and two PAH mutants by pre-equilibrating each ligand for 10 min prior to addition of ferrous ion and BH4/DTT as described in enzyme reaction protocol in order to assess for ligand-induced PAH inhibition or activation. Overall, PAH activity was measured in triplicate (n=3) by CE based on the average relative peak area ratio of Tyr to IS, whereas the reproducibility of three biological replicates performed over three days was found to be acceptable with an overall CV under 10% (n=9).

Primary Assay for PC Screening Based on Enzyme Enhancement in Urea—

Unlike thermal stability assays that can induce protein aggregation, chemical denaturants are more suitable as perturbants to promote unfolding and enzyme inactivation while solubilizing multimeric proteins. In this context, restoration of enzyme activity upon denaturation (READ) was first introduced to characterize PCs that stabilize yet enhance the activity of a lysosomal enzyme, β-glucocerebrosidase (GCase). Herein, READ was modified, further optimized and validated for primary screening of PCs for the cytosolic enzyme (PAH) using a chemical library containing structurally unique compounds with drug-like activity. For instance, the primary screen was used to measure ligand-induced stabilization of PAH by extrinsic small molecules that impart greater resistance to urea unfolding as compared to ligand-free apo-enzyme conditions. PAH activity was first examined as a function of urea concentration (0 to 8 M) and pre-equilibration time (10 min to 2 hr) in order to determine optimum conditions where residual enzyme activity was largely attenuated below 10% due to protein unfolding. Protein unfolding was performed in triplicate offline with the enzyme reaction buffer (20 mM HEPES and 200 mM NaCl, pH 7.0) using tetrameric human PAH (1 µM and/or 0.1 µM) or mutant PAH (1 µM and/or 0.1 µM) incubated 10 min in 0 M or 8 M urea in the presence or absence of ligand (20 µM). Dose-response studies (0, 2.0 and 20 µM) were subsequently performed in triplicate on screen-positive compounds using re-synthesized ligands in order to further validate initial screen results. In all cases, quenched enzyme reactions were processed as described previously prior to CE analysis. PAH activity measurements based on Tyr formation at 8M urea with the presence or absence of PC were normalized to 0 M urea for each aliquot enzyme reaction to minimize long-term variation, which also enables direct comparison of the ligand-induced stabilization activity under denaturing conditions (8M urea) while confirming inhibition and activation effects for ligands under native conditions (0 M urea).

Confirmation Testing of Chaperone Activity Upon Enzyme Refolding—

A secondary assay was developed to directly measure chaperone activity of screen-positive compounds in terms of ligand interactions that enhance recovery of PAH activity after protein unfolding. A stronger chemical denaturant than urea, GndCl, was required in this case in order to perturb PAH structure and conformation to a greater extent as a way to significantly attenuate enzyme activity upon refolding. For instance, a recovery of 50% of residual enzyme activity was achieved without ligand when PAH was incubated in 8.0 M urea after its dilution to 0.5 M urea to trigger protein refolding. In order to further reduce enzyme reversibility, the recovery of PAH activity was subsequently assessed when it was incubated using 6.0 M GndCl for 10 min and subsequently diluted to 0.5 M GndCl in the presence or absence of screen-positive ligands (20 µM) in enzyme reaction buffer with PAH activity measurements performed by CE as described previously. In this case, WT-PAH was found to regain approximately (7±0.5) % residual activity (three biological replicates, CV<10%) when it was initially incubated at 6 M GndCl for 10 min then subsequently diluted to 0.5 M GndCl as compared to PAH activity measured at 0.5 M GndCl, where the enzyme exists in a folded and active state. Two lead compounds and several analogs of SA were subsequently tested using two different mutants of PAH (I65T and R261Q) without chemical denaturants after the two-tiered screening.

Results and Discussion

Optimization of Separation Conditions for Tyr Quantification—

In this work, an enzyme kinetic assay for functional screening of PCs was developed for accurate quantification of PAH-catalyzed Tyr formation using CE with UV detection. Full resolution of all components of the quenched enzyme reaction is achieved by CE as shown in FIG. 1, including excess substrate (Phe, 1 mM), product (Tyr), oxidized/reduced forms of cofactor (BH4/BH2), buffer (HEPES) and IS (Me-Tyr). Tyr formation was measured in a reaction containing both Phe and BH4, whereas no product formation is detected in a negative control without BH4 as required for enzyme activity. On-line sample pre-concentration was used in CE to enhance concentration sensitivity notably when using narrow internal diameter fused-silica capillaries (25 µm) to improve separation efficiency under high voltages with fast analysis times (<4 min). Table 1 summarizes the major analytical merits of the CE assay for enzyme kinetic studies of PAH, which was found to have excellent linearity, reproducibility and adequate sensitivity while using low amounts (≈1 pmol) of recombinant enzyme. Moreover, greater selectivity and lower detection limits (LOD≈1.0 µM) are achieved by CE with conventional UV absorbance as compared to nitrosonaphtol derivatization of Tyr with fluorimetric detection. Indeed, a 30-fold lower detection limit can also be achieved for Tyr when using CE with laser-induced native fluorescence detection.

TABLE 1

Summary of CE assay for assessment of PAH activity

| Figures of merit | L-Tyr |
|---|---|
| Linearity ($R^2$) | 0.9995 |
| Linear Range | 2.5-1000 µM |
| Intra-day assay precision (% CV) | 3.0 |
| Inter-day assay precision (% CV) | 5.7 |
| Sensitivity ($\mu M^{-1}$) | 0.0068 (±0.0001) |
| Limit of detection (S/N ≈ 3) | 1.0 µM |
| Limit of quantification (S/N ≈ 10) | 2.5 µM |

Optimization of a Functional Two-Tiered PC Screening Method for PAH—

Figure 2:
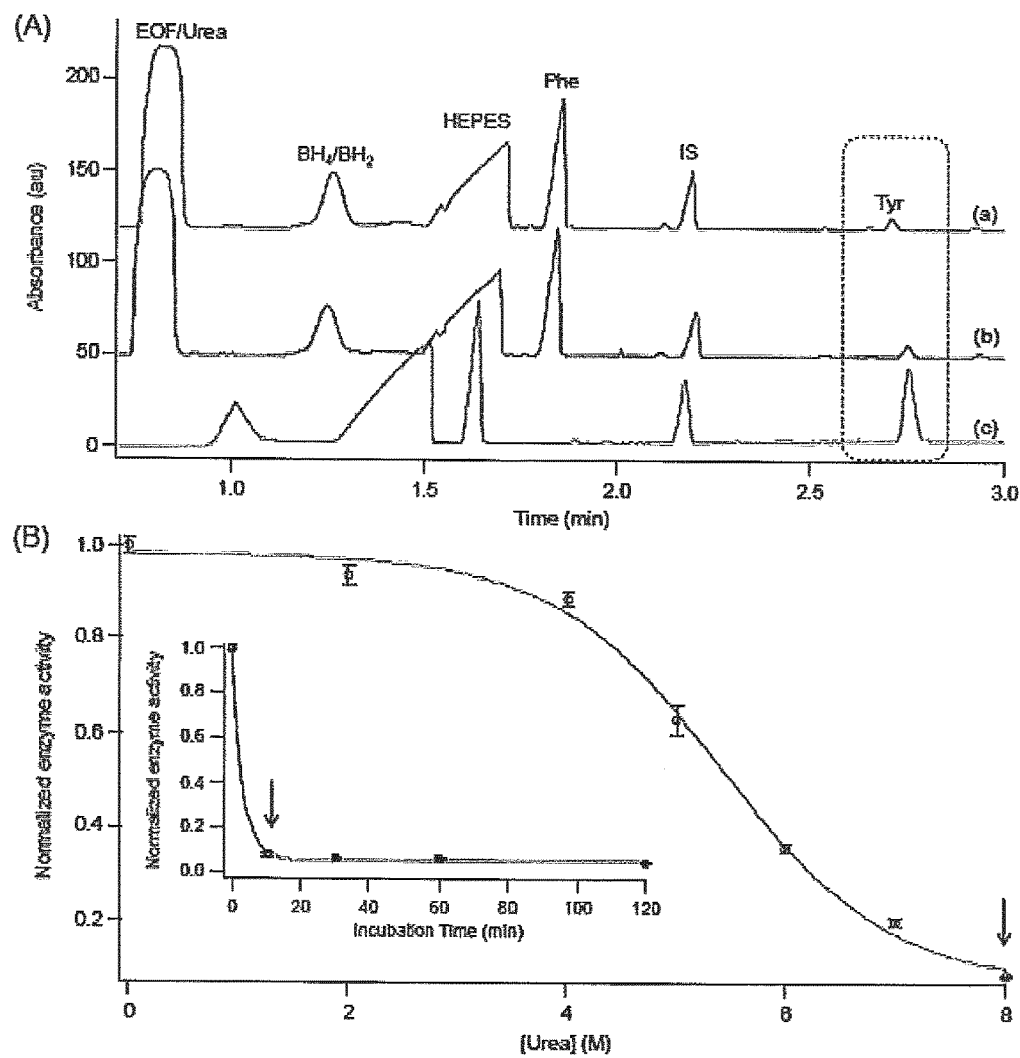
FIG. 2 illustrates (A) a series of electropherograms depicting the loss in enzymatic activity of PAH upon denaturation in urea. Tyr formation was significantly attenuated in 8 M urea after (a) 10 min or (b) 60 min incubation relative to (e) 0 M urea conditions for the wild-type/folded enzyme in a stabilization assay, and (B) a PAH activity curve as a function of urea concentration highlights that only about 7% of residual activity remains at 8 M urea with rapid unfolding occurring within 10 min of equilibration.

Since inhibitor potency or ligand binding affinity is not always directly associated with increases to protein conformational stability, a label-free CE assay was developed for characterization of changes in PAH catalytic activity upon ligand association, Primary screening methods also rely on WT enzymes for PC candidate selection under native conditions, which contributes to potential bias during follow-up testing on various PAH mutations associated with the PKU disease spectrum with loss in function pathogenesis due to reduced stability. In this context, READ was used as high-quality screening method for PCs that measures enzyme activity enhancement due to ligand-induced stabilization under denaturing conditions with chemical denaturants. Herein, READ was further modified and optimized for better selection of PCs for PAH from a small library containing structurally novel synthetic compounds. PAH activity was initially monitored as a function of urea concentrations (0 to 8 M) with pre-equilibration times ranging from 10 min to 2 hr prior to initiation of enzyme reaction. FIG. 2 demonstrates that Tyr formation by WT-PAH was significantly attenuated when pre-equilibrated using 8 M urea with rapid protein unfolding within 10 min that did not change over 1 hr. In this case, CE also resolves excess urea that co-migrates with the electro-osmotic flow (EOF) as a neutral solute without spectral interferences impacting Tyr quantification. Overall, the normalized activity of WT-PAH was reduced to only (7.0±0.5) % (under these conditions (8 M urea/10 min) relative to the native/folded enzyme without urea. Since WT-PAH was found to regain about half of its catalytic activity upon dilution of urea without extrinsic ligands, protein refolding was performed using a stronger denaturant, GndCl in order to perturb PAH structure to a greater extent in order to mimic a severe mutation associated with a significant loss in catalytic activity. As a result, the reversibility of WT-PAH activity was monitored when pre-equilibrated with various concentrations of GndCl (4-8 M) for 10 min and subsequently diluted to 0.5 M GndCl (data not shown). In this case, WT-PAH was found to retain only about (7±0.5) % when using 6.0 M GndCl for 10 min followed by dilution to 0.5 M GndCl where the activity is normalized to enzyme at 0.5 M GndCl concentration (data not shown). Unlike thermal denaturation techniques (e.g., isothermal calorimetry) that often induce irreversible precipitation of multimeric protein, solubilizing chemical denaturants enables direct characterization of the chaperone potential of ligand binding that assists in the refolding of denatured/mutant enzyme in order to significantly enhance the residual activity of PAH.

This two-tiered screening method when used to identify PCs that target phenylalanine hydroxylase (PAH) and using capillary electrophoresis (CE) with UV detection, enabled label-free characterization of enzymatic activity upon refolding via L-tyrosine (Tyr) formation kinetics. This functional assay directly measured PAH activity with short analysis times (<3 min), low detection limits (S/N≈3, 1.0 µM) and good inter-day precision (CV<10%) without spectral interferences.

Discovery of Novel PCs for PAH from a Chemical Library—

A hundred drug-like compounds were pre-selected via in-silico screen from an in-house chemical library comprising six hundred structurally unique synthetic compounds based on Lipinski's rule of five, including MW<500 Da, log P<4, HBDs<5, HBA<10 and TSPA<120 Å$^2$. In-silico screen minimizes false discoveries during primary screening by eliminating compounds that have undesirable properties such as insolubility and cytotoxicity. A primary screen using CE was first performed based on ligand-induced stabilization of WT-PAH activity under denaturing conditions for identification of putative PC candidates at a 20 µM dosage level. Screen-positive compounds were selected if they induced a significant enhancement in PAH activity exceeding a 8% cut-off since ligand-free enzyme was found to retain only (7±0.5) % residual activity at 8 M urea. In addition, PC candidates were selected provided they did not induce significant WT-PAH inhibition (<20%) under native conditions without urea, such as the competitive inhibitor F-Phe that was used as a screen-negative control in this work. FIG. 3(a) depicts a plot that compares the measured activity of WT-PAH under native and denaturing conditions for a sub-group of 7 lead candidates with putative PC activity. In most cases, these compounds did not display any measurable enzyme inhibition at 20 µM with two ligands (e.g., 5-H4 and SA) having weak activation effects on WT-PAH. Moreover, three compounds (e.g. MMP, 2-E7 and 5-H4) were found to enhance WT-PAH residual activity by over 3-fold (>21%) under denaturing conditions. PC selectivity was evaluated by including competitive and mixed-type inhibitors to β-glucocerebrosidase that is associated with Gaucher disease such as isofagomine, ambroxol, diltiazem and fluphenazine, which showed no enhancement effect on PAH activity (data not shown). In addition, two recently reported PCs for PAH, 3-amino-2-benzyl-7-nitro-4-(2-quinolyl)-1,2-dihydroisoquinolin-1-one (compound III) and (5,6-dimethyl-3-(4-methyl-2-pyridinyl)-2-thioxo-2,3-dihydrothieno [2,3-d] pyrimidin-4(1H)-one (compound IV) were included as positive controls in this work since they were reported to stabilize PAH by shifting denaturation temperatures greater than 14° C. and 7° C. at 100 µM relative to ligand-free enzyme, respectively.

Compounds III and IV at 20 µM increased PAH residual activity to 19% and 9% of WT-PAH in comparison to lead candidates identified from the chemical library, including SA, 5-H4, 2-E7 and MMP which increased enzyme activity to 16, 21, 25 and 35% residual activity of WT-PAH, respectively, as shown in FIG. 3a. Five lead compounds that function as significant stabilizers of PAH without undesirable inhibition from the primary screen were subsequently tested for chaperone activity by measuring changes in enzyme activity upon ligand association after dynamic protein refolding upon dilution from 6.0 M to 0.5 M GdmCl. In this case, FIG. 3b demonstrates that two compounds (MMP, SA) were found to induce a 3 and 5-fold increase in WT-PAH activity relative to ligand-free apo-PAH enzyme, respectively. Differences in ligand ranking as measured by a two-tiered screening strategy for PCs highlights that they probe distinct binding interactions associated with ligand-induced stabilization of the native state enzyme (i.e. primary screen) as compared to stabilization of the PAH tetramerization process and/or partially unfolded intermediates during protein refolding (i.e. secondary screen). FIG. 3c highlights the dose-response effect on measured Tyr formation by CE with UV detection as related to increases in WT-PAH activity when comparing equimolar doses (2 and 20 μM) of MMP and SA relative to ligand-free apo-enzyme. Similarly, compounds III and IV were found to increase the residual activity of WT-PAH after refolding by about 5- and 1.5-fold, respectively. The latter two molecules were previously shown to enhance the thermal stability and activity of PAH in vitro, as well as the steady-state levels of PAH in-vivo. Compound IV acts as a weak competitive inhibitor to PAH ($K_i$=200 μM) unlike other related tyrosine and tryptophan hydroxylase enzymes while enhancing the folding of the PAH tetramer similar to BH4. Although three compounds, 1-H8, 2-E7 and 5-H4 were weak activators or stabilizers of WT-PAH under native or denaturing conditions (FIG. 3a), they did not display any significant chaperone activity when using the refolding assay (FIG. 3b). Thus, the optimum PC candidates for subsequent testing with PKU-mutants activate, stabilize and assist refolding of WT-PAH in a dose-response dependent manner, such as SA.

Structure-Activity Relationships for Shikimic Acid Analogs—

Figure 3:
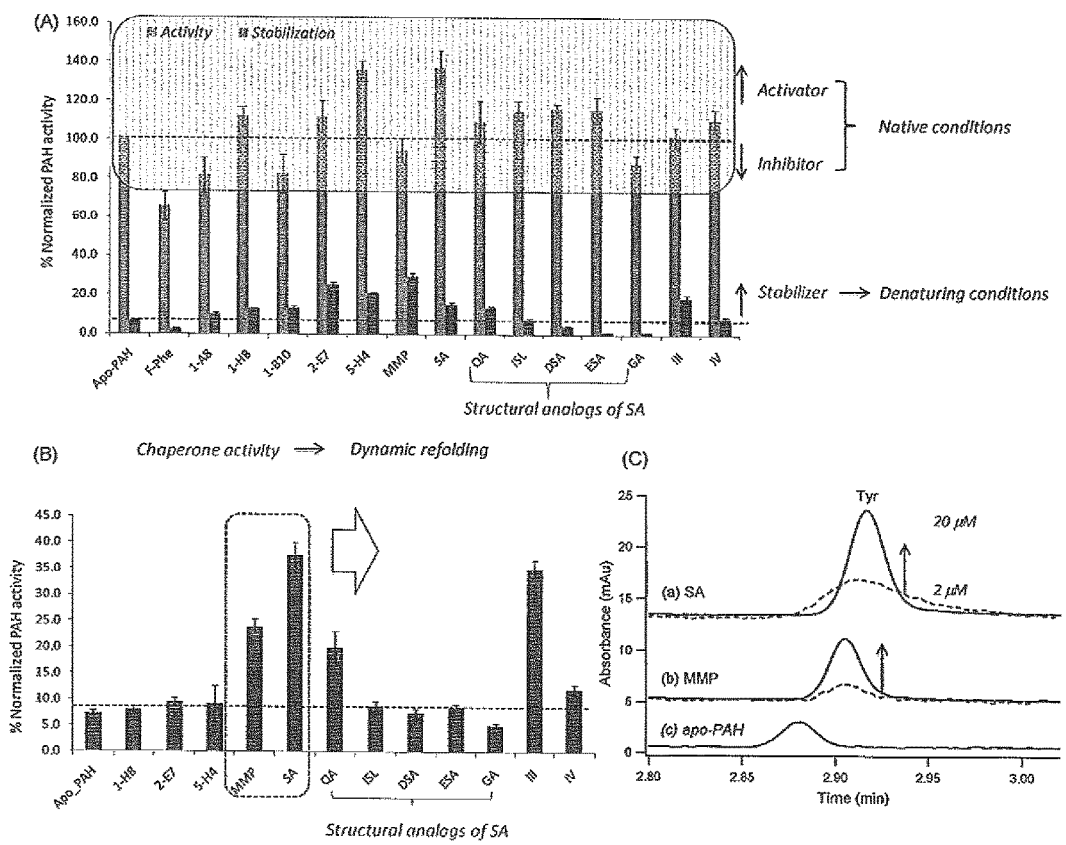
FIG. 3 graphically illustrates shows the identification of PC candidates for PAH based on two-tiered functional assay, including (A) Primary screening of representative PCs derived from a chemical library with drug-like properties (100 compounds, 20 µM) under native/folded (0 M urea, activity) relative to denaturing/unfolded conditions (8 M urea), (B) Chaperone activity by dynamic refolding studies of PAH after dilution from 6.0 M to 0.5 M GdnCl with the presence of PCs, lead compounds (MMP, SA and QA) significantly restored. Compounds III and V are screen-positive controls previously determined to have PC activity for PAH. (C) Chaperone potency is graphically indicated by a dose-dependent enhancement in residual PAH activity that is restored in presence of 20 μM of SA or MMP by three and five-fold relative to apo-PAH, respectively, where error represents ±1σ with precision (n=6) under 10%.
Figure 4:
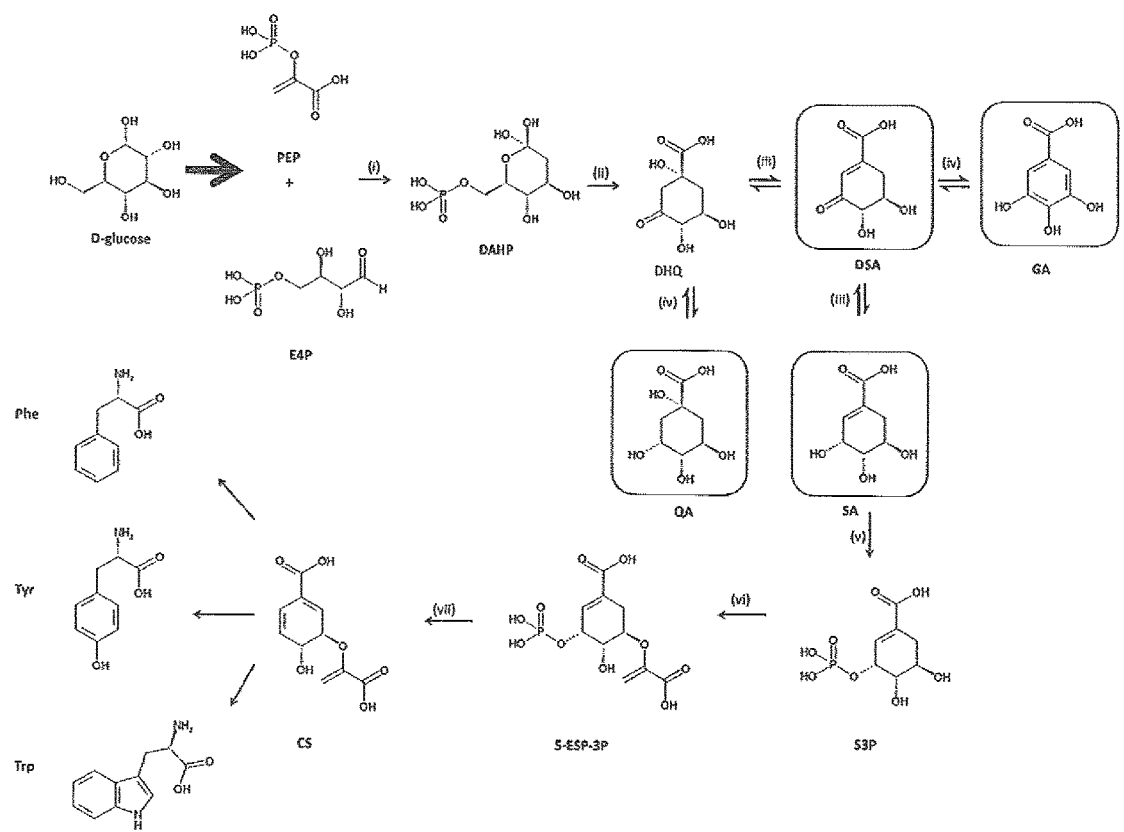
FIG. 4 shows the biosynthesis of the aromatic amino acids in plants and microbes via the shikimic acid (SA) pathway. Enzymes involved in synthesizing intermediates are as follows: (i) 3-deoxy-D-arabino-heptulosonic acid 7-phophate synthase, (ii) 3-dehydroquinate synthase, (iii) 3-dehydroquniate dehydratase, (iv) shikimate dehydrogenase, (v) shikimate kinase, (vi) 5-enolpyruvylshikimate-3-phosphate synthase (vii) chrosmate synthase. Intermediates from each step are: Phosphoenolpyruvate (PEP), D-erythrose-4-phosphate (E4P), 3-deoxy-D-arabino-heptulosonic acid-7-phosphate (DAHP), 3-dehydroquinate (DHQ), 3-dehydroshikimic acid (DSA), quinic acid (QA), shikimic acid (SA), shikimate-3-phosphate (S3P), 5-enolpyruvylshikimate-3-phosphate (5-EPS-3-P), chofismate (CS), phenylalanine (Phe), tyrosine (Tyr), tryptophan (Trp). SA and structural analogs of SA that were used in structural-activity relationship studies for WT and mutant PAHs are highlighted as a key intermediate in this metabolic pathway.
Figure 5:
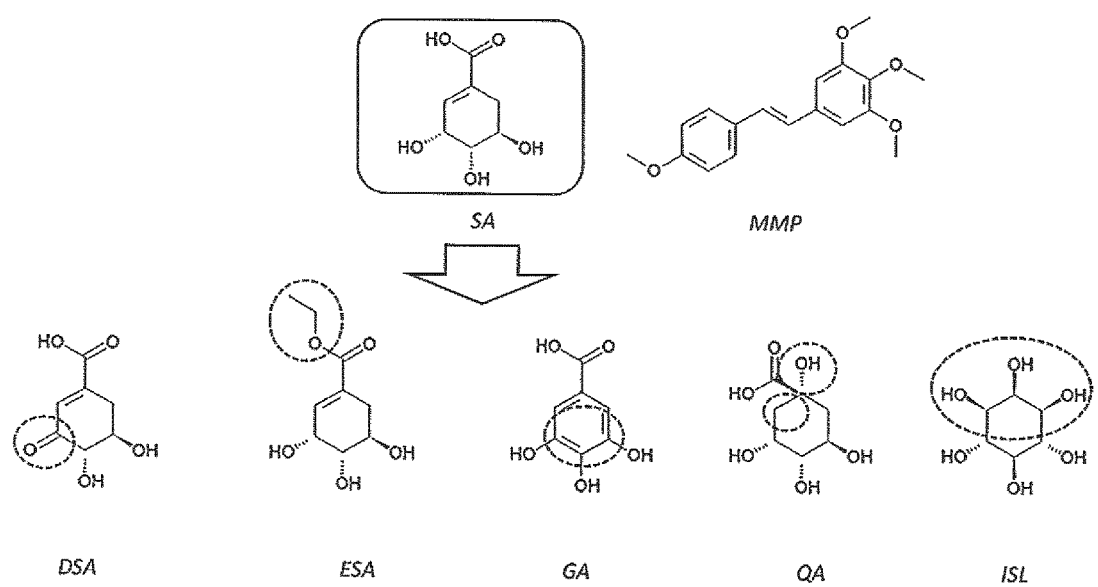
FIG. 5 shows the structure of shikimic structural analogs. Structures of two PCs (MMP & SA) based on "two-tiered" functional assay approach using WT-PAH. Structural analogs of SA, 3-dehydroshikimic acid (DSA), ethoxyshikimate (ESA), gallic acid (GA), D-(−)-quinic acid (QA), myo-inositol (ISL). Modifications of functional group moiety from parent compounds SA are highlighted in dotted circle.

Due to the remarkable properties of SA that assists in protein refolding to enhance the residual activity of WT-PAH from (7±0.5) % to about (38±2) %, several other SA analogs were also explored to identify structural motifs associated with its unique chaperone activity. Indeed, SA is a key intermediate in the biosynthesis of aromatic amino acids (FIG. 4) that also serves as a precursor to lignin and numerous bioactive secondary metabolites in plants and microbes. Due to the absence of the shikimate pathway in mammals, it also represents a key target in medicinal chemistry. For instance, 6-fluoro-shikimate, is a synthetic SA analog used as an antimicrobial agent that acts as a competitive inhibitor ($IC_{50}$=15 μM) of *Plasmodium falciparum*. Also, the aromatic polyphenol analog of SA, gallic acid (GA) which is synthesized via shikimate dehydrogenase from 3-dehydroshikimic acid (DSA) inhibits oligomerization of beta-amyloid peptide. FIG. 5 depicts the chemical structures of five different SA analogs that were examined for their ability to stabilize the native enzyme and/or enhance residual PAH activity upon refolding. FIG. 3 demonstrates that D-quinic acid (QA) was a structural analog that also exhibits PAH stabilization and chaperone activity. This suggests that the reduction of the double bond and hydroxylation at C-1 does not significantly alter reversible ligand binding interactions with WT-PAH. QA is a major plant-derived component in the human diet recently shown to induce biosynthesis of tryptophan and nicotinamide by microflora in the gastrointestinal tract. In contrast, oxidation of the 3-hydroxyl moiety (DSA) and esterification of the carboxylic acid (ethoxyshikimate, ESA) abolishes the chaperone activity as measured for SA, whereas GA in fact destabilizes and reduces the activity of WT-PAH upon refolding. Similarly, myo-inositol (IST) is a cyclic polyol analog of SA and major renal osmolyte shows no significant activity at 20 μM for stabilizing WT-PAH. These observations indicate that the stereo chemistry of the three polyol moieties and the weak acidity of the carboxylic group are motifs which preserve favourable interactions with WT-PAH without unwanted inhibition. The lack of SA inhibitory effects on WT-PAH suggests allosteric binding to WT-PAH unlike the majority of PCs reported to date. Moreover, the wide distribution of SA and QA in nature suggests that these well-tolerated plant-derived metabolites are safe for human consumption since they are aromatized by gut microflora and excreted as hippuric acid in urine.

Confirmatory Testing of Lead PC Candidates with PKU-Mutants—

Figure 6:
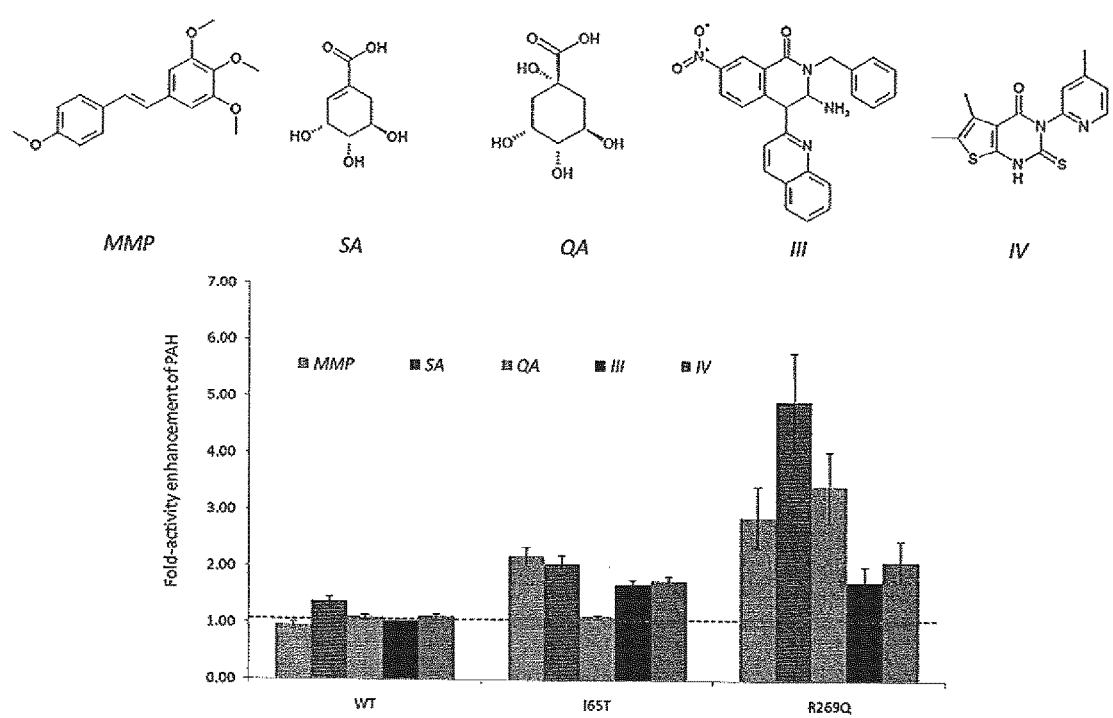
FIG. 6 graphically shows the validation of PCs with PKU-mutants. Stabilization effect of two hits (MMP & HCH) and two reference compounds were tested with WT and two PKU-mutants (I65T and R261Q) of PAH. MMP showed 2-fold activity enhancement with I65T mutant form whereas HCH showed 5-fold increased activity with R269Q mutant form. The two reference compounds (HI and IV) showed about a 1.5-fold activity enhancement with the both mutant forms of PAH that is consistent with results based on cell-based assays. Error represents a σ±1 (n=3).

MMP, SA and QA and two reference compounds (III and IV) were further tested with two PKU mutants due to their significant ligand-induced stabilization and activity enhancement effects on WT-PAH. This is to validate whether the two-tiered in-vitro screen relying on unfolded/inactive WT-PAH under denaturing conditions is sufficient to indicate activity towards clinically relevant mutant enzymes associated with the PKU disease spectrum. Two clinically relevant PAH mutants, I65T and R261Q were selected without chemical denaturants by measuring changes in Tyr formation by CE after ligand association. For instance, the I65T mutation is proposed to distort the hydrophobic packing in the regulatory domain core and is associated with mild to moderate PKU phenotypes, whereas R261Q mutation affects the structure of PAH and exhibits highly variable PKU from mild-moderate-severe form. It was previously reported that a modest increase in PAH activity with BH4 oral supplementation induces a 2.5-fold higher rate in Phe oxidation in certain patients with mild PKU despite conflicting data caused by large between-subject differences in responsiveness. QA, MMP and SA at 20 μM enhanced the activity of I65T PAH mutant from 1.2- to 2-fold, whereas a 3- to 5-fold enhancement in R261Q PAH mutant was measured in this work as shown in FIG. 6. Also, 2-E7 was included as a screen-negative control, which showed no measurable activity enhancement for either PAH mutant at 20 μM (data not shown). In comparison, compounds III and IV were found to include a 1.6 to 2.0-fold enhancement in both PKU-mutants at the same dosage level. Despite using a new CE-based functional assay to measure ligand-induced increases to PAH activity in-vitro, this data is consistent since compounds III and IV were recently reported to induce a 1.2 to 2.0-fold enhancement in activity of PKU-mutants (I65T and R261Q) in A293 cells while inducing a 2-fold enhancement in PAH activity in WT mouse liver. Overall, SA displayed the greatest chaperone activity notably for the more severe mutant (R261Q) retaining only 5% residual PAH activity, which is well above the therapeutic threshold reported for the efficacy of BH4 supplementation. Unlike BH4, SA offers a cost-effective option for PC therapy for treatment of PKU since it is a widely sought after natural product in the food, cosmetic and pharmaceutical industry that can be manufactured by large-scale microbial fermentation processes. Moreover, QA is a common plant-derived metabolite found in the human diet.

In summary, PAH activity was determined by accurate quantification of Tyr formation using a selective, sensitive yet label-free CE-based assay with UV detection. A functional two-tiered screening strategy was developed and validated for discovery of novel PCs for PAH from a chemical library comprising structurally unique compounds with drug-like activity. Using this strategy, compounds were found which activate, stabilize and assist with refolding of denatured WT-PAH, which were demonstrated to have significant chaperone activity for two PKU-mutants relative to reference compounds with known activity in-vivo. For example, SA was found to induce an unprecedented 3-5 fold enhancement in WT-PAH activity, as well as two PKU-mutants. This is the first example of a natural product that functions as a weak activator and PC for WT and mutant enzymes without unwanted inhibition. Ultimately, SA or analogues thereof, alone or in a combination therapy with, for example, BH4, may provide better overall efficacy for treatment of mild to severe PKU phenotypes that overcomes quality of life, costs and compliance issues of Phe-restriction diets.

The invention claimed is:

1. A method of restoring phenylalanine hydroxylase activity in mammalian phenylalanine hydroxylase comprising exposing said phenylalanine hydroxylase to shikimic acid, a pharmaceutically acceptable salt of shikimic acid, a functionally equivalent analogue thereof selected from the group of:
   i) an analogue of shikimic acid having one or more additional substituents on the cyclohexene ring of shikimic acid, wherein the additional substituent is selected from the group consisting of hydroxyl, thio, —$OR^1$, —$NH_2$, $NO_2$, —$NHR^1$, —$NR^1R^2$, —$SR^1$ and a $C_1$-$C_6$ alkyl group, $C_1$-$C_6$ alkoxy, and $C_1$-$C_6$ alkanol, wherein $R^1$ and $R^2$ are independently selected from the group consisting of $C_1$-$C_6$ alkyl, $C_1$-$C_6$ alkanol and $C_1$-$C_6$ alkoxy;
   ii) an analogue in which one or more of the hydroxyl groups on the cyclohexene ring of shikimic acid is substituted with hydrogen, thio, $C_1$-$C_6$ alkyl, $C_1$-$C_6$ alkanol, $C_1$-$C_6$ alkoxy, —$OR^1$, —$NH_2$, $NO_2$, —$NHR^1$, —$NR^1R^2$, or —$SR^1$; and
   iii) an analogue in which the cyclohexene ring of shikimic acid is replaced with a cyclohexane ring;
or combinations thereof.

2. The method of claim 1, wherein the phenylalanine hydroxylase is denatured.

3. The method of claim 1, wherein the phenylalanine hydroxylase is a mutant enzyme.

4. The method of claim 3, wherein the mutant is selected from the I65T mutant and the R261 Q mutant.

5. The method of claim 1, wherein the phenylalanine hydroxylase is exposed to an amount of shikimic acid or salt or analogue thereof in the range of about 0.2 μM to 20 mM.

6. The method of claim 1, wherein the analogue is D-quinic acid or a pharmaceutically acceptable salt thereof.

7. A method of treating phenylketonuria in a mammal comprising administering to the mammal a therapeutically effective amount of shikimic acid, a functionally equivalent analogue thereof selected from the group of:
   i) an analogue of shikimic acid having one or more additional substituents on the cyclohexene ring of shikimic acid, wherein the additional substituent is selected from the group consisting of hydroxyl, thio, —$OR^1$, —$NH_2$, $NO_2$, —$NR^1R^2$, —$SR^1$ and a $C_1$-$C_6$ alkyl group, $C_1$-$C_6$ alkoxy, and $C_1$-$C_6$ alkanol, wherein $R^1$ and $R^2$ are independently selected from the group consisting of $C_1$-$C_6$ alkyl, $C_1$-$C_6$ alkanol and $C_1$-$C_6$ alkoxy;
   ii) an analogue in which one or more of the hydroxyl groups on the cyclohexene ring of shikimic acid is substituted with hydrogen, thio, $C_1$-$C_6$ alkyl, $C_1$-$C_6$ alkanol, $C_1$-$C_6$ alkoxy, —$OR^1$, —$NH_2$, $NO_2$, —$NHR^1$, —$NR^1R^2$, or —$SR^1$; and
   iii) an analogue in which the cyclohexene ring of shikimic acid is replaced with a cyclohexane ring;
a pharmaceutically acceptable salt of shikimic acid or analogue thereof, or combinations thereof.

8. The method of claim 7, wherein the amount of shikimic acid or salt or analogue thereof is-administered to the mammal is in the range of about 0.2 μM to 20 mM.

9. The method of claim 7, wherein the analogue is D-quinic acid or a pharmaceutically acceptable salt thereof.

* * * * *